(12) United States Patent
Pidgeon et al.

(10) Patent No.: US 6,562,627 B1
(45) Date of Patent: May 13, 2003

(54) HIGH THROUGHPUT METHOD FOR MEASUREMENT OF PHYSICOCHEMICAL VALUES

(75) Inventors: Charles Pidgeon, West Lafayette, IN (US); Jianming Yin, Brighton, MA (US); Nadege Rooke, Framingham, MA (US); Ling Han Morgan, Brighton, MA (US)

(73) Assignee: BDC Pharma LLC, Chicago, IL (US)

( * ) Notice: Subject to any disclaimer, the term of this patent is extended or adjusted under 35 U.S.C. 154(b) by 0 days.

(21) Appl. No.: 09/471,854

(22) Filed: Dec. 23, 1999

Related U.S. Application Data

(60) Provisional application No. 60/113,441, filed on Dec. 23, 1998.

(51) Int. Cl.$^7$ ............................................... G01N 30/02
(52) U.S. Cl. ...................... 436/161; 436/103; 436/501; 422/69; 422/70; 210/198.2
(58) Field of Search .................. 436/161, 501, 436/103; 422/70, 69; 210/198.2

(56) References Cited

U.S. PATENT DOCUMENTS

| | | | |
|---|---|---|---|
| 4,683,213 A | * 7/1987 | Ax ............................... | 436/501 |
| 4,927,879 A | 5/1990 | Pidgeon | |
| 4,931,495 A | 6/1990 | Pidgeon | |
| 5,310,688 A | * 5/1994 | Zale et al. .................... | 436/535 |
| 6,054,047 A | * 4/2000 | Hindsgaul et al. ........ | 210/198.2 |
| 6,139,735 A | * 10/2000 | Wainer et al. ............ | 210/198.2 |

FOREIGN PATENT DOCUMENTS

| | | |
|---|---|---|
| WO | WO 99/10522 | 8/1998 |

OTHER PUBLICATIONS

Pidgeon Solid phase membrane mimetics: Immobilized artificial membrances, Enzyme Microb. Technol. 1990, vol. 2 (2), pp. 149–150.*

Robards et al, "High–Performance Liquid Chromatography–Separations," Academic Press ISBN 0–12–589570–4, pp. 342–344 (1994), Month Unavailable.

Waksmundzka–Hajnos M., "Chromatographic Separations of Aromatic Carboxylic Acids," Journal of Chromatography B, vol. 717, pp. 93–118 (1998), Month Unavailable.

Berg et al., "Interfacial Catalysis by Phospholipase $A_2$: Determination of the Interfacial Kinetic Rate Constants," Biochemistry, vol. 30, pp. 7283–7297 (1991), Month Unavailable.

Berg et al., "Thermodynamic and Kinetic Basis of Interfacial Activation: Resolution of Binding and Allosteric Effects on Pancreatic Phospholipase $A^2$ at Zwitterionic Interfaces," Biochemistry, vol. 36, pp. 14512–14530, (1997).

Berg et al, "Interfacial Activation of Triglyceride Lipase from *Thermomyces* (*Humicola*) *lanuginosa*: Kinetic Parameters and a Basis for Control of the Lid," Biochemistry, vol. 37, No. 19, pp. 6615–6625 (1998).

Yang et al., "Immobilized Artificial Membranes–Screens for Drug Membrane Interactions", Advanced Drug Delivery Reviews, vol. 23, pp. 229–256, (1996).

(List continued on next page.)

*Primary Examiner*—T. Tung
*Assistant Examiner*—Yelena Gakh
(74) *Attorney, Agent, or Firm*—Barnes & Thornburg

(57) ABSTRACT

Methods are provided for determining a dissociation constant for each one of at least a portion of a set of compounds. The methods include contacting a solution of the set of compounds with a membrane mimetic surface exhibiting a non-specific compound-dependent affinity for at least the portion of the compounds. A parameter dependent on the non-specific affinity of the surface for each one of at least the portion of the set of compounds in the test solution is measured and used to calculate the dissociation constant.

32 Claims, 7 Drawing Sheets

OTHER PUBLICATIONS

Julian et al., "A Method for Quantitatively Differentiating Crude Natural Extracts Using High–Performance Liquid Chromatography–Electrospray Mass Spectrometry," Anal. Chem., vol. 70, No. 15, pp. 3249–3254 (1998).

Kassel et al., "Automated Analytical/Preparative High–performance Liquid Chromatograpy–mass Spectrometry System for the Rapid Characterization and Purification of Compound Libraries," J. Chrom. A., vol. 794, pp. 3–13 (1998).

Moore et al. "Peak–decay method for the measurement of dissociation rate constants by high–performance affinity chromatography", J. Chromatogr., 1987, v. 384, pp. 91–103.*

Munro et al. "Expermental and theoretical studies of rate constant evalution by affinity chromatography. Determination of rate constants for the interaction of saccharides with concanacalin A", J. Chromatogr., 1993, v. 646, pp. 3–15.*

Hardcastle et al. "Determination of dissociation constants of polyprotic acids from chromatographic data", J. Chromatogr. B, 1998,, v. 717, pp. 39–56.*

* cited by examiner

CHROMATOGRAPHIC FINGERPRINT FOR
HALLUCINOGEN MAF$^\mu$ VECTOR

CHROMATOGRAPHIC FINGERPRINT FOR BDFA
COMPARED TO THAT OF HALLUCINOGEN MAF$^\mu$
VECTOR (*)

FIG. 5

HIGH THROUGHPUT METHOD FOR MEASUREMENT OF PHYSICOCHEMICAL VALUES

CROSS REFERENCE TO RELATED APPLICATIONS

This application claims priority under 35 U.S.C. § 119(e) to U.S. Provisional Patent Application Ser. No. 06/113,441, filed on Dec. 23, 1998.

This invention relates to a rapid, high throughput method for simultaneously measuring biologically significant physicochemical characteristics for multiple compounds. More particularly, this invention is directed to the measurement and use of binding affinities of multiple compounds with a surface under controlled conditions to calculate biologically significant physicochemical values. In one embodiment, the present invention provides a new method for the determination of a most important biological parameter, membrane interfacial $^{surface}$pKa, the knowledge of which significantly facilitates understanding of drug-membrane interactions and thereby speeds the drug discovery process.

BACKGROUND AND SUMMARY OF THE INVENTION

Many potential new drug candidates are created every year, and both pharmaceutical and biotechnology industries have embraced the challenge in recent years of developing faster and more efficient ways to screen pharmaceutical compounds in order to rapidly identify "hits" and develop them into promising lead drug candidates. This has created the need for high-throughput analytical approaches to characterize the synthesized compounds and has prompted the development of chromatographic systems specifically designed for the automated high-throughput identification, purity assessment, purification or determination of the physicochemical properties of the compounds in combinatorial libraries.

With the advent of combinatorial chemistry and the need to develop assays for the large numbers of compounds being made available using that technology, many researchers have focused their efforts on developing in vitro tests/assays that provide biologically significant compound information. Much work has been directed to correlation of certain physicochemical properties with biological activity, both in the search for new therapeutic agents and in the understanding of compound toxicity both from medicinal and environmental perspectives.

The rise of combinatorial chemistry and other drug discovery technologies has vastly increased the number of new compounds to be evaluated as potential drug candidates. Accordingly, new high-throughput strategies are required to evaluate compound properties beyond potency and selectivity. A major focus in the pharmaceutical industry is to develop new drugs with good oral bioavailability. Bioavailability represents both the quantity of the drug administered reaching the blood circulation, and the rate of this phenomenon. It has been generally considered that the bioavailability of an orally administered drug is mostly determined by its physicochemical properties; e.g., its molecular weight, pKa, lipophilicity, solubility. One of the factors influencing oral bioavailability is the gastrointestinal pH, as it influences the ionization of the compounds. Most drugs are either weak bases or weak acids, and normally only the non-ionized fraction (i.e., the most lipophilic form) crosses biological membranes, except when transport carriers are involved. It becomes evident that knowledge of the pKa of potential drug candidates may give insight as to how good an oral bioavailability they will exhibit. In particular, having access to the dissociation state of said drug candidates at the membrane interface ($^{surface}$pKa) would be helpful, as it would give an indication on their potential oral bioavailability and thus their pharmaceutical value. Thus, one physicochemical property of recognized significance to evaluation of a compound's biological activity, whether it be therapeutic efficacy or toxicity, is its dissociation constant, more significantly, the dissociation constant exhibited by the compound at a membrane interface.

For an ionizable compound, the degree of dissociation (or protonation) in solution is usually quantified by the pKa value of the acidic form. Thus, in the following acid-base equilibrium equation.

$$HA \rightleftharpoons A^- + H^+$$

the dissociation constant Ka is expressed as:

$$K_a = \frac{[H^+][A^-]}{[HA]}$$

The pKa of a molecule, defined as $-\log K_a$, is indicative of its degree of ionization, or of its acidic strength in solution. To be able to predict the extent to which a particular compound will ionize at a given pH (for example at physiological pH) is of great importance because it will give insight as to how well the substance in question will be able to participate in physical, chemical and biological reactions. A prominent example from medicinal chemistry is the ability of drugs to pass through biological membranes as well as their potential to interact with intracellular receptors, both of which are affected by the readiness of the drug to undergo protonation or deprotonation. Many biological processes involve reactions at the surface of, or within, cell membranes. Explanation of these functions in structural terms requires a physicochemical understanding of the various interactions taking place. In many cases the processes concern small amphiphilic molecules with pKa values close to physiological pH, and therefore both charged and uncharged forms may interact with the membrane. At the membrane surface, each form partitions into the membrane to a different extent, depending on the respective membrane affinities (FIG. 2). The membrane-bound solute species are in turn involved in yet another acid/base equilibrium, with a dissociation constant $^{surface}$Ka distinct from the above mentioned $^{bulk}$Ka. The $^{surface}$pKa (interfacial/surface pKa) is frequently biologically relevant, as it is the true indicator of the ionization state of the solute at the membrane interface, and therefore provides fundamental information of the solute/membrane interactions.

Several studies have demonstrated the key role that solute ionization plays in solute/membrane interactions. Biological membranes are made up of a lipid bilayer, which is a complex mixture of lipids and proteins held together mainly by non-covalent interactions. In such mixtures, phase separation leading to domain formation is possible, where the lipids are not distributed uniformly but rather in "clusters". The domains' surfaces differ in physicochemical properties, and a particular chemical (drug) is expected to have different membrane binding and partitioning behaviors (dictated in part by its $^{surface}$pKa) with the membrane domains. This may contribute to accumulation and co-localization of receptors and drugs in the same (small and specialized) membrane region. It has been shown that solute ionization can determine the depth of membrane penetration and location of solutes in membranes, as well as affect the membrane physiology. The local anesthetic tetracaine hydrochloride (TTC) is a good example, because at pH 5.5 the positively charged TTC resides near the phospholipid head group region, whereas at pH 9.0 the uncharged TTC penetrates more deeply into the hydrocarbon region of the membrane. This membrane penetration behavior significantly affects the expansion of the membrane, which has been proposed as one aspect of the mechanism of action of anesthetics. This study not only demonstrates that membrane physiology is affected by charged versus neutral molecules, but also that the activity of the compound, and the depth of its membrane penetration depend on its ionization state at the membrane surface and not in the bulk solution.

In addition to affecting the location of molecules in cell membranes, solute ionization also affects solute movement from the outer monolayer to the inner monolayer of cell membranes: for example, it has been reported that the migration of unionized fatty acids across the phospholipid bilayer is much greater than for their ionized counterparts. The rapid flip-flop of unionized fatty acids has important physiological implications as it enables the rapid entry and removal of fatty acids from cells such as adipocytes, hepatocytes, and heart muscle tissue. Movement between the inner and outer monolayer of cell membranes is necessary for transport not only of fatty acids but also many biologically important compounds. For example it has been reported that the ability of certain CNS compounds to cross the blood-brain barrier is affected by their ionization state. The antiarrhythmic aminoxylidides have a pKa ranging from 4.8 to 8.0. Assuming a constant overall concentration of the drug and a physiological pH of 7.4, the concentrations of the ionized forms of the drug molecules could vary by as much as 2.5 logarithmic units, and 0.7 log unit for the unionized species. That study emphasizes that any changes in pKa can lead to a dramatic difference in concentration of the drug molecules at the membrane surface. This also demonstrates the importance of the interfacial pKa as a useful predictive parameter of a drug's potential activity, toxicity and ability to transport through the membrane bilayer.

Solute ionization also influences the binding energy between solutes and cell membranes, which is an important parameter associated with the transport of solutes across membranes. Finally, and probably most importantly, the solute's ionization state can play a critical role in the biological activity of the molecule in question. For example, the activity of protein kinases C (PKC) requires the presence of negatively charged acidic phospholipids. One putative mechanism to inhibit protein kinase C is to neutralize negatively charged phospholipids at the cell membrane. N,N-Dimethyl-D-sphingosine (DMS), a known inhibitor of PKC and a potential antitumor agent, has a membrane bound pKa value of 8.8. As a result of this high pKa, 90% of DMS is protonated at physiological pH which causes inhibition of PKC activity. Other analogs in the sphingosine family also display this charge dependent inhibitory activity. The key point is that the ionized DMS species is believed to be the active chemical species and understanding solute ionization may allow similar conclusions for other compounds. Being able to determine whether the ionized versus unionized species is biologically active may thus be important to drug design.

Similarly, the degree of ionization is an important factor for the toxicity and fate of organic compounds in natural waters, and specific modes of toxic action, such as the uncoupling of oxidative phosphorylation, depend directly on both the lipophilicity and the acidity of the chemical compound. The bioavailability of chemical contaminants in the environment is governed by physicochemical properties and chemical reactivity, which also determine their ability to bioaccumulate and exert certain modes of toxic action in organisms. Knowing the pKa of a particular compound is important because it gives a partial understanding of its partitioning and concentration in the surrounding biological systems and thus gives insights about its ecotoxic potential. The degree of ionization of a chemical can affect its ability to bind to certain soils and sediments, or its interaction with certain living organism cell membranes and thus its toxicity. For example, the aquatic toxicity of several chlorophenols and nitrophenols has been evaluated in different biological systems (bacteria, plant, and fish among others). These phenolic compounds are known to be oxidative uncouplers, and in eukaryotic species, the mechanism of that action is believed to be by destruction of the electrochemical membrane potential by carrying protons into mitochondria, thus depleting the energy needed for ATP formation. Thus pKa is an important parameter capable of predicting the potential environmental toxicity of chemicals. Such knowledge is also valuable from the practical viewpoint of implementing and surveying water quality criteria for instance.

Another aspect also related to toxicity is exemplified by chemicals as toxic gases, synthetic chemicals, cosmetics and topical medicines, which have the ability of entering the body through the skin. These percutaneous transport processes are heavily dependent on the ionization state of the compounds under consideration. The skin permeability of chemicals is associated with their ionization state which affects their potential toxicity.

The classical method for the calculation of bulk pKa is given by the Hammet equation, which is based on the classification of the compound of interest into a parent structure with substituents of known increment values. The determination of pKa's by this method is straightforward and has been routinely used in structure-activity analyses to evaluate the impact of ionization on bioaccumulation or toxicity. However, application of this classical method is principally restricted to certain types of parent structures and substituents, which may not apply to the compound under investigation. Capillary electrophoresis has also been used for the determination of pKa in solution.

Liquid chromatography-high resolution electrospray mass spectrometry (LC-ESI-MS) has been used for the identification of known and unknown synthetic peptides for peptide sequencing and characterization. The peptides were enzymatically digested using trypsin and the digests analyzed by LC-ESI-MS. The structurally similar peptides resulted in the formation of a number of common tryptic fragments. These tryptic fragments were not always resolved chromatographically for each peptide, but it was possible to select representative CAD (collisionally activated dissociation)-MS spectra from the data and enable amino acid sequencing of the tryptic fragments.

Julian et al. (Julian, R. K. Jr., Higgs, R. E., Gygi, J. D., Hilton, M. D., "A Method for Quantitatively Differentiating Crude Natural Extracts Using High-Performance Liquid Chromatography-Electrospray Mass Spectrometry." *Anal. Chem.*; 70(15); 3249–3254 (1998)) developed a system that was based on recent advances in chemical analysis and computation to quantitatively characterize and compare complex chemical mixtures. They tested the system on fermentation extracts for drug screening are from 88 uncharacterized fungi. The chemical analysis system is comprised of a pair of HPLC systems to take turns separating the chemical constituents detected by ESI-MS. The system was distinguished from earlier applications of LC-MS in that it was comprised of three components: (a) HPLC separation of the analytes, (b) ESI-MS detection of effluent analytes, and (c) a computational tool to allow effective comparison of the large data sets that are generated by the analysis.

Kassel et al. (L. Zeng, L. Burton, K. Yung, B. Shushan, D. B. Kassel, "Automated analytical/preparative high-performance liquid chromatography-mass spectrometry system for the rapid characterization and purification of compound libraries." *J. Chrom. A.*, 794:3–13 (1998)) reported an automated parallel analytical/preparative HPLC/MS workstation to increase the analysis speed for characterizing and purifying combinatorial libraries. The system incorporated two columns operated in parallel for both LC/MS analysis and preparative LC/MS purifications. This technique provided a better match for the speed of parallel synthesis. The authors are working on a system with four analytical or preparative columns operated in parallel.

Both spectroscopic and non-spectroscopic methods have been developed to measure $^{surface}$pKa. Spectroscopic methods include fluorescence, nuclear magnetic resonance (NMR), and electron spin resonance (ESR). Non-spectroscopic methods include dialysis and surface activity measurement.

For chemically diverse groups of compounds, all of these methods have significant limitations. For instance, fluorescence requires that compounds have a pH-sensitive fluorescent functional group that can be used to quantitate the fraction ionized and unionized at the membrane surface. This is rarely the case. With the exception of fluorescent probes specifically designed to measure the polarity of membrane surfaces, very few solutes possess a fluorescent functional group. ESR methods require spin labeled functional groups that no biologically relevant solute possesses. NMR methods usually have a problem with sensitivity, and consequently milligram quantities of isotope-labeled compounds need to be prepared for each compound. However, the most significant limitation is that most spectroscopic methods have been developed only for Type-1 compounds which exhibit very large membrane partition coefficients such that the solutes are quantitatively membrane-associated at the equilibrium partitioning condition. Except for ESR, spectroscopic methods usually cannot be used for Type-2 compounds that have significant amounts of solute in both the aqueous and membrane environment at the equilibrium partitioning condition. Regarding non-spectroscopic methods like dialysis, which can be used for the latter type of compounds, these methods are experimentally tedious, time consuming, and several measurements are needed to obtain the interfacial pKa. Propagation of error in the experimental measurement also makes the final pKa liposome measurement contain a large amount of uncertainty.

Due to the significant influence of ionization on the location, transport, binding, and activity of molecules, quantitating the ionization state of chemical species by measuring the pKa of membrane associated solutes provides fundamental information that increases our understanding of membrane physiology and solute/membrane interactions. No general method for measuring the pKa of solutes bound to membranes exists. In addition, there is no commercially efficient method that requires minimum amounts of compounds or that allows the high volume determination of bulk pKa's as is needed today for screening the large number of compounds being made available in combinatorial chemical libraries.

The present invention is directed to a method for determining a physicochemical value for each compound of a set of compounds, such as those that comprise a combinatorial chemical library. The method comprises dissolving the compounds in a plurality of liquid media to form a multiplicity of test solutions of the set of compounds. Each test solution then contacts a surface under a pre-determined set of conditions of temperature and/or pressure. A parameter dependent on the affinity of the surface for each compound in each test solution is measured after contact of the solution with the surface under the pre-determined set of conditions. The measured parameters are then used to calculate the physicochemical value according to a pre-determined algorithm. The present invention provides a method for utilizing chromatographic systems for high-throughput analyses of the physicochemical properties of distinct compounds in a set of compounds. This method allows such determinations to be made in a highly efficient and rapid manner.

BRIEF DESCRIPTION OF THE DRAWINGS

FIG. 5 is a comparison between two chromatograms to demonstrate the use of peak width as a parameter for determination of physicochemical characteristics.

DETAILED DESCRIPTION OF THE INVENTION

Figure 1:
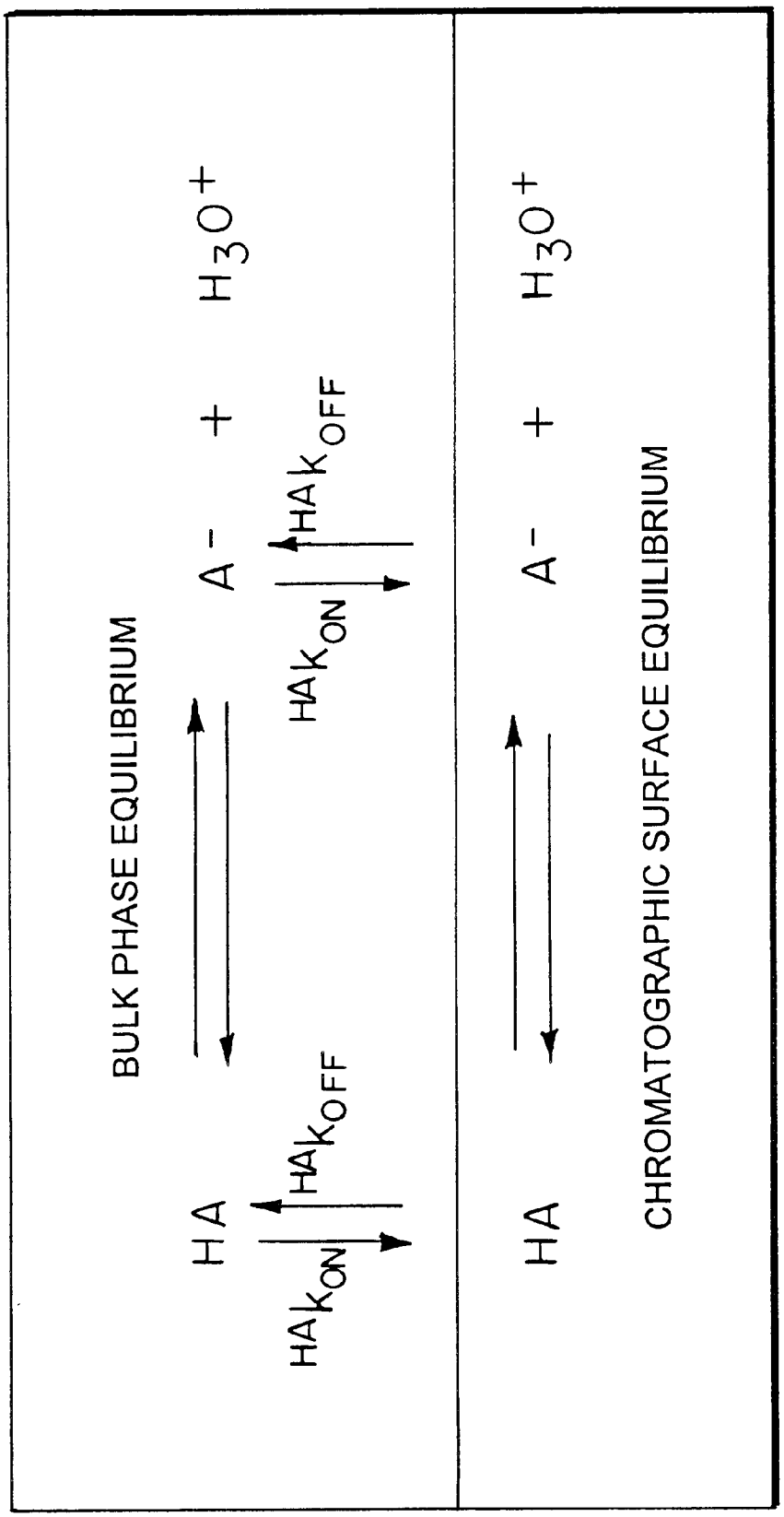
FIG. 1 depicts equilibrium partition coefficients of solutes partitioning between chromatographic surface and the bulk aqueous media.

The present invention is directed to a method for determining a physicochemical value for each compound of a set of compounds, such as those that comprise a combinatorial chemical library. The method comprises dissolving said compounds in a plurality of liquid media, each liquid medium having a pre-determined composition, to form a multiplicity of test solutions of the set of compounds. Each test solution is then contacted with a surface under a pre-determined set of conditions of temperature and pressure. The surface is selected such that it exhibits a compound-dependent affinity for each compound. The affinity can be of a specific or non-specific nature. A parameter dependent on the affinity of the surface for each compound in each test solution is measured after contact of the solution with the surface under the pre-determined set of conditions. The measured parameters are then used to calculate the physicochemical value according to a pre-determined algorithm. Typically at least a portion of the compounds tested are compounds having a known value for the physicochemical characteristic being calculated. Preferably the method is implemented using liquid chromatography, more preferably high pressure liquid chromatography, to carry out the step of contacting each test solution with the surface. The stationary phase comprises the surface, the aqueous medium is the mobile phase, and the affinity-dependent parameter is the retention time for each compound.

One embodiment of the present invention is a method requiring minimal experimental effort for the high throughput simultaneous determination of both $^{bulk}$pKa and $^{surface}$pKa of compounds. The method for determining pKa involves dissolving a set of compounds in a plurality of aqueous media, each having a unique hydrogen ion concentration to form a multiplicity of test solutions of said compounds (also having unique hydrogen ion concentrations). Each of the test solutions is then contacted with a surface exhibiting a compound-dependent affinity for the dissolved compounds and then a parameter dependent upon the affinity of the surface in each solution for each of the compounds may be calculated after the compounds are evaluated by analysis of each solution after it is contacted with the surface. The dissociation constant for each compound is then calculated from the pH-dependent measured parameters for each respective compound. In one embodiment, the test solution is prepared so that the solute compounds are at substantially equimolar concentrations. For the purpose of describing this invention, "substantially equimolar concentrations" includes equimolar ±20%.

The step of contacting each test solution with the surface can be carried out by contacting a predetermined volume of each test solution with a pre-determnined area of said surface, and the affinity-dependent parameter for each compound is its concentration in each test solution after equilibrium contact with the surface. In another more preferred embodiment, the step of contacting each solution with the surface is carried out by liquid chromatography using a stationary phase and a liquid mobile phase wherein the stationary phase comprises the surface and the aqueous medium is the mobile phase. In such embodiments the test solutions having unique hydrogen ion concentrations are effectively formed in the chromatographic column with the aqueous medium mobile phase. The term "aqueous" as used herein means containing water in some portion. The aqueous media of the present invention can optionally include at least a portion of an organic modifier, such as water-miscible organic solvents and water dispersable surfactants. The affinity-dependent parameter can be the retention time for each compound. Alternatively, the mobile phase can be delivered as a pH gradient. The surface can be selected from a wide variety of commercially available chromatographic supports. One preferred class of surfaces is a membranous or membrane mimetic surface comprising phospholipids covalently bound to a solid substrate.

The classical method for determining $^{bulk}$Ka's experimentally is titration. This requires the need for significantly higher quantities of the test compounds to do the measurement. More importantly, it requires that the compound be completely soluble in the solvent (water) before the titration is carried out. Thus, for compounds with poor water solubility, a modified aqueous medium has to be used and the $^{bulk}$Ka's obtained cannot be easily compared between compounds(because$^{bulk}$pKa's depend on the medium composition). The present method circumvents this problem. If a compound is not soluble in water, the sample can be prepared in an organic solvent (or a mixture of organic solvent and aqueous solution) and injected onto the chromatographic column.

Because the sample size is so small, the chromatographic system can be run with 100% aqueous mobile phase and still be solubilized. In other words, even though a compound may have poor water solubility, the method allows the measurement of both $^{bulk}$pKa and $^{surface}$pKa under 100% aqueous conditions when it is impossible with the titration method.

Chromatography will provide the capacity factors k' of each of the many compounds detected upon elution from the column, at (for example) various mobile phase pH's. Correlation of the capacity factors with the pH of the mobile phase allows the calculation of the $^{bulk}$pKa and $^{surface}$pKa for each compound. The chromatographic method is fast, convenient, and of wide scope, as it can by applied to any chromatographic substrate surfaces whether commercially available or custom designed. Further, use of a chromatographic system allows for high-throughput analyses of a plurality of chemical compounds, thus increasing the rapidity and efficiency with which physicochemical properties can be determined for a large number of compounds. Access to the interfacial pKa of a wide variety of chemicals with numerous types of surfaces is therefore possible. The choice of chromatographic surfaces will depend upon the compounds for which the $^{surface}$pKa is to be determined, whether the effects of such compound be biological, purely chemical, or environmental.

A mass spectrometer coupled to a chromatographic system insures an accurate and efficient detection and identification of the compounds eluting from the chromatographic column. Each fraction will be analyzed and its composition determined, so that each compound identified (MS) will be associated with a retention time (chromatography). The LC-MS method will allow concomitant identification of the compounds and determination of their capacity factors (and thus their $^{bulk}$pKa's and $^{surface}$pKa's).

In another embodiment, there is provided a method for measuring a thermodynamic property of each compound in a set of compounds. The method comprises dissolving the set of compounds in a liquid medium to form a test solution. The test solution is then contacted with a surface/interface exhibiting a compound-dependent affinity for said compound at least two separate temperatures. A parameter dependent on the affinity of the surface for each compound at each temperature is then measured using, for example, mass spectrometric analysis. The measured parameters are then used in a pre-determined algorithm to calculate the temperature dependent property of at least a subset of the compounds. Thus, for example, values for enthalpy, entropy and free energy can be calculated based on values for affinity-related parameters as a function of temperature.

The chromatographic process represents a reversible equilibrium of solutes between the mobile phases and the stationary phases. The magnitude of solute retention is a direct result from this equilibrium and is typically expressed by a parameter, the capacity factor, k'. The capacity factor is therefore a stoichiometric mass distribution of solute between the stationary phases and the mobile phases. For ionizable compounds the ionized form and unionized form of solutes reach an equilibrium state in both the mobile phases and the stationary phases (see FIG. 1). In this situation the solute retention is assumed to occur as the summation of interactions of ionized and unionized solutes within the mobile phases and the stationary phases. These interactions are organized into an equation and expressed as followed.

$$k' = \{k'_0 + k'_{-1}(K_a/[H^+])\}/\{1+(K_a/[H^+])\} \qquad \text{Eq. 1}$$

where k' is the capacity factor of a partially dissociated solute, k'$_0$ and k'$_{-1}$ are the capacity factors of the neutral and anionic forms of the solute, respectively, and Ka and [H⁻] are the acidity constant and proton activity, respectively. The plot of capacity factor vs. pH is a sigmoidal curve with a midpoint pH that equals the pKa value of the solute tested (FIG. 4).

This k'/pH correlation has been reported for a set of phenolic and nitrogen-containing compounds. An octadecyl-bonded silica gel column was used for this study. The retention time of these compounds were measured by HPLC at 40° C. in 70% aqueous acetonitrile containing 20 mM sodium phosphate buffer. All buffer solutions have a pH range of 2–12. The data were collected and the capacity factor values were calculated using the following equation, $$k'=\{t_r-t_0\}/t_0 \qquad \text{Eq. 2}$$

where $t_0$ is the dead time and $t_r$ is the retention time.

Figure 4:
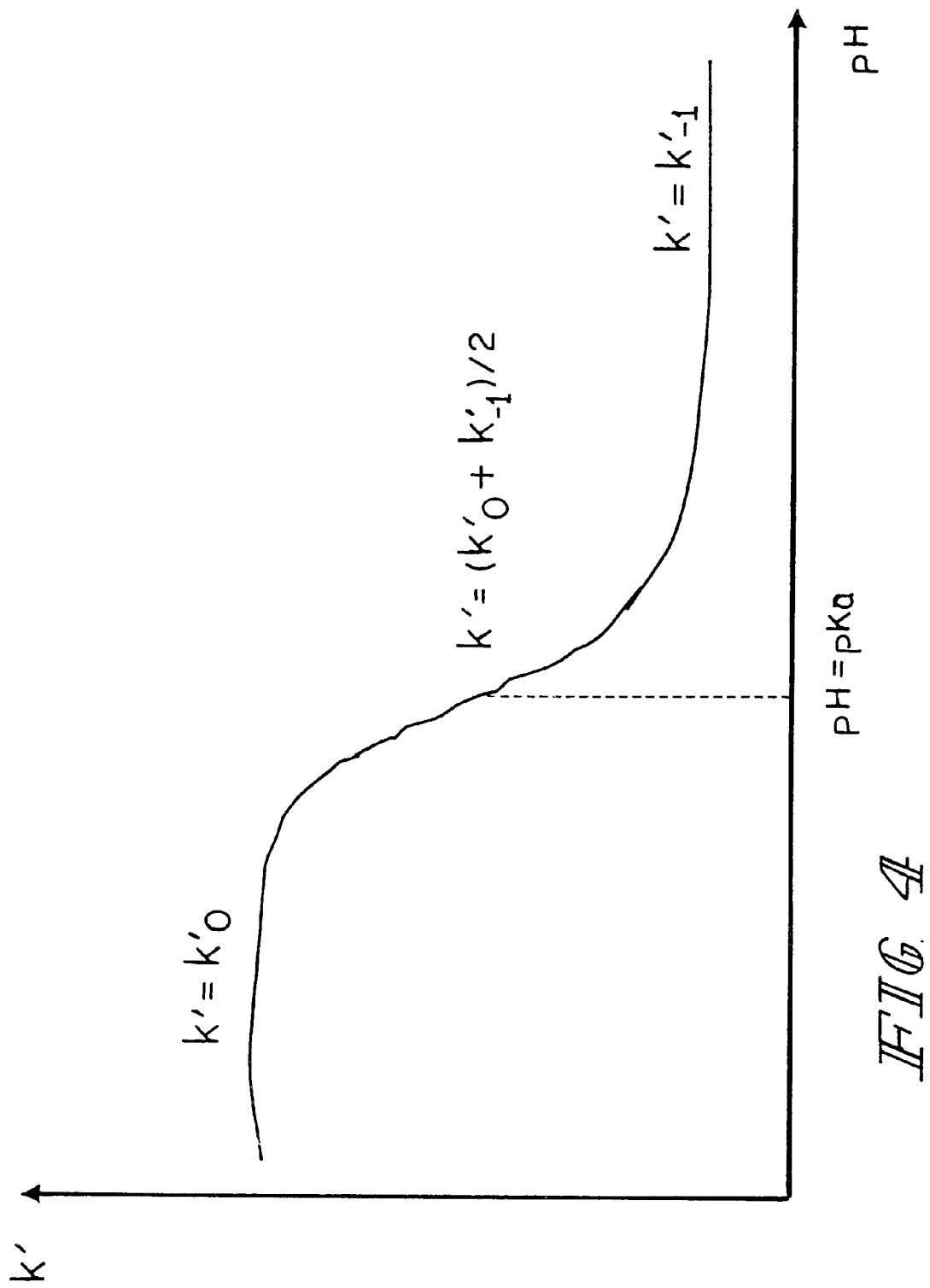
FIG. 4 is an exemplary plot of the capacity factor(k') versus the pH of the eluent in a chromatographic method in accordance with this invention.

The plot of capacity factor (k') as a function of pH value based on Equation 2 is shown in FIG. 4 as a sigmoidal curve. At low pH, where only neutral acid exists in solution, k' equals $k'_0$. At high pH, only anions of the acid exist in solution, and k' equals $k'_{-1}$. When k equals $(k'_0+k'_{-1})/2$, the pH equals pKa. Therefore, the pKa value equals the midpoint pH value and can be obtained directly from the plot of k' versus pH.

The standard deviations of the acidity constants by this method are typically within 0.09 pKa units. The dielectric constant changes in the solvent will have effects in acidity constants on the compounds. The advantages of this method over others are that only 1 mg or less of the substance is needed for the acidity constant determination and that the purity of the substance is not critical if the impurity can be separated from the substance studied on the reverse phase chromatography column. If the pKa value is lower than 3 or higher than 11, the accuracy of this method will decrease because of the error introduced by the pH measurement itself and the uncertainty associated with the drawing of the upper or the lower portions of the capacity factor vs. pH plots.

LC-MS is an exceptional method with high sensitivity, specificity and speed. Some of the recent LC-MS applications have been for protein structural characterizations, natural product extracts differentiation, and rapid characterization and purification of combinatorial synthesis libraries. In one preferred embodiment of this invention, the use of LC-MS is extended to rapid high throughput measurements of bulk pKa and interfacial $^{surface}$pKa and other parameters.

Theoretical Derivatization of Bulk and Interfacial pKa's.

For the measurement of $^{surface}$pKa, a more general equation is needed, where both $^{surface}$pKa and $^{bulk}$Ka values can be obtained experimentally and computationally. The method developed for use in accordance with the present invention is based on the general definition for solute ionization as it applies, or occurs, at the surface and in the bulk aqueous solution. The equilibrium ionization at the surface for a monoprotic acid HA can be quantitated by $^{surface}$Ka according to $$^{surface}Ka=^{surface}[A^-][H^+]/^{surface}[HA] \qquad \text{Eq. 3}$$

For the equilibrium ionization in the bulk solution, the following equation exists $$^{bulk}Ka=^{bulk}[A^-][H^+]/^{bulk}[HA] \qquad \text{Eq. 4}$$

where $^{surface}[A^-]$ and $^{surface}[HA]$ are the concentration of the ionized and unionized species at the chromatographic surface, $^{bulk}[A^-]$ and $^{bulk}[HA]$ are the concentration of the ionized and unionized species in the bulk aqueous solution, respectively, and $[H^+]$ is the proton concentration in the bulk solution, i.e., the mobile phase.

The membrane partition coefficient ($K_{app}$) of a solute on surfaces is defined as $$K_{app}=(^{surface}[A^-]+^{surface}[HA])/(^{bulk}[A^-]+^{bulk}[HA]) \qquad \text{Eq. 5}$$

substituting $^{surface}[A^-]$ and $^{bulk}[A^-]$ from eq. 3 and eq. 4 into eq. 5 gives $$K_{app}=K_{HA}([H^+]+^{surface}Ka)/([H^+]+^{bulk}Ka) \qquad \text{Eq. 6}$$

where $K_{HA}$ is the membrane partition coefficient of the protonated HA species, $^{surface}Ka$ is the membrane interfacial ionization constant of the compound tested, and $^{bulk}Ka$ is the ionization constant of the compound in the bulk aqueous phase. Since $K_{app}/\beta=k'_{app}$ and $K_{HA}/\beta=k'_{HA}$ ($\beta$ is a constant for a given column), eq. 6 divided by $\beta$ gives $$k'_{app}=k'_{HA}([H^+]+^{surface}Ka)/([H^+]+^{bulk}Ka) \qquad \text{Eq. 7}$$

where $k'_{app}$ is the capacity factor of the test compound measured at different mobile phase pH conditions, and $k'_{HA}$ is the capacity factor of the non-ionized species. Nonlinear fitting of the three experimentally measured parameters [H+], $k'_{app}$, and $k'_{HA}$ to eq. 7 can be used to obtain numerical estimates for both $^{surface}Ka$ and $^{bulk}Ka$ of the compound. This method is particularly useful for compounds with a high $^{bulk}Ka$. For compounds with low $^{bulk}Ka$ a similar equation can be derived which is $$k'_{app}=k'_A^-([H^+]^{surface}K_a+1)/([H^+]^{bulk}K_a+1) \qquad \text{Eq. 8}$$

The reason for developing eq. 7 is that eq. 7 is useful for basic compounds and eq. 8 is useful for acidic compounds when the $^{bulk}Ka$ of the compound is not known. To satisfy high throughput requirements, note that $k'^{HA}$ (for eq. 7) or $k'_A^-$ (for eq. 8) do not need to be experimentally measured for $^{bulk}Ka$ and $^{surface}Ka$ to be determined. Both parameters ($k'_{HA}$ and $k'_A^-$) can be treated as unknowns in the equations (like $^{bulk}Ka$ and $^{surface}Ka$), and the experimental data can be used to calculate (by non-linear curve fitting) three parameters ($k'_{HA}$ (or $k'_A^-$) and $^{bulk}Ka$ and $^{surface}Ka$) instead of two ($^{bulk}Ka$ and $^{surface}Ka$). This reduces the number of experimental data to be collected, and still allows the determination of the desired parameters ($^{bulk}Ka$ and $^{surface}Ka$).

With reference to FIG. 1, HA denotes the neutral species of a monoprotic acid and A⁻ the unionized species as shown in FIG. 1. The rapid on/off rates of HA and A⁻ cause the bulk phase equilibrium to be coupled to the ionization equilibrium at the chromatographic surface and therefore one peak elutes even though multiple chemical species exist during the separation process. During any chromatographic separation, solute binding to the chromatographic surface is considered to be the primary equilibrium event. All other equilibria are treated as secondary because binding to the chromatographic surface controls both solute retention and resolution. Thus for a weak acid HA the solute-to-surface on/off process for HA is theoretically distinct from A⁻, and he primary equilibrium for HA and A⁻ are shown in FIG. 1. The other ionization equilibrium between HA and A⁻ in the mobile phase and at the immobilized artificial membrane (IAM) surface are considered to be secondary equilibria from a chromatographic perspective. Ionization in bulk solution is rapid and NMR measurements indicate that the equilibrium at membrane surfaces is faster than the NMR time scale. Thus, both the primary and secondary equilibria shown in FIG. 1 are sufficiently fast that a single chromatographic peak is observed when weak acids or base are chromatographically analyzed. Although a single peak elutes, the pH dependent solution profile of acids and bases has been used to measure $^{bulk}$pKa values and then extend this theory to measure $^{surface}$pKa. One hypothesis is that $^{surface}$pKa=$^{liposome}$pKa when surfaces and liposomes are prepared from the same lipids.

Figure 2:
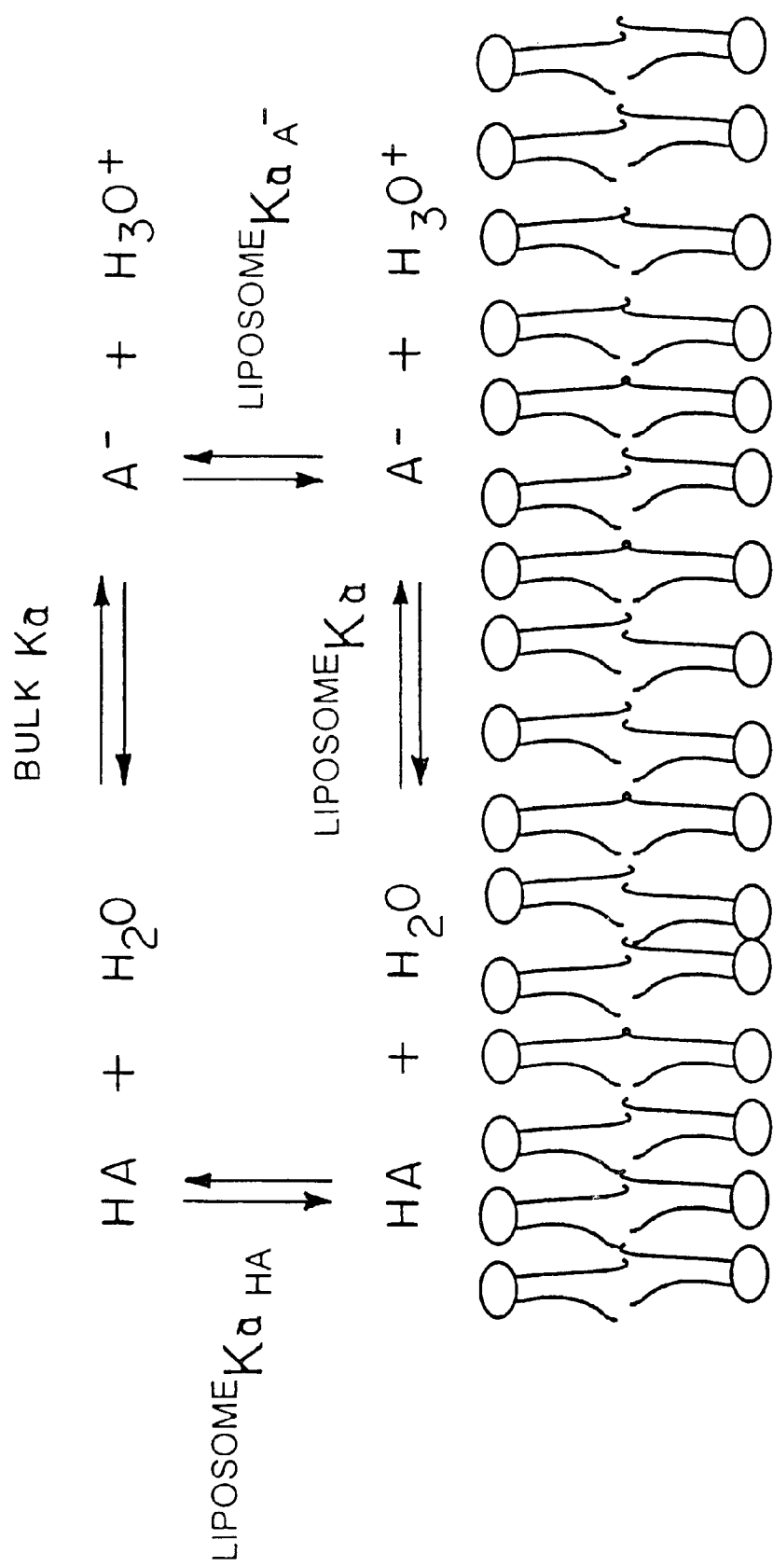
FIG. 2 is similar to FIG. 1 and illustrates that the ionization equilibria in the bulk solution and the membrane surface are coupled through the partition coefficients of the ionized ($A^-$) and unionized (HA) chemical species.

FIG. 2 depicts the same thermodynamic factors that control solute ionization also control partitioning and consequently there is a direct relationship between membrane partition coefficients and $^{bulk}$Ka. Thus, theoretically, by merely measuring the liposome partition coefficient of the ionized and unionized species, $^{liposomes}$pKa can be directly calculated if $^{bulk}$pKa is known.

Figure 3:
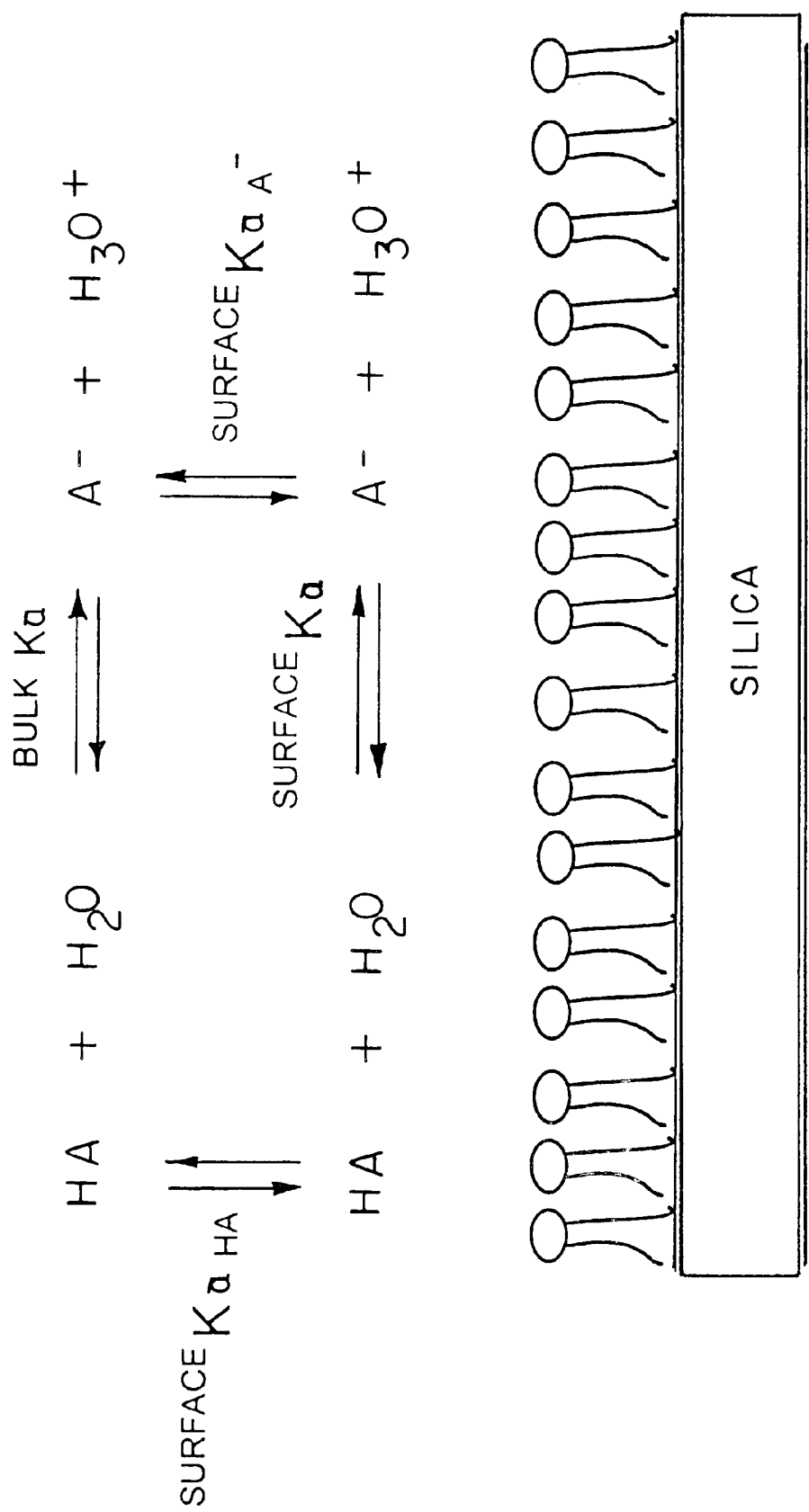
FIG. 3 is similar to FIGS. 1 and 2 and illustrates that the ionization quilibria in the bulk solution and a chromatographic surface are coupled through the partition coefficients of the ionized ($A^-$) and unionized (HA) chemical species.

FIG. 3 depicts the concept that the chromatographic surfaces may act as solid phase models of liposome membranes. If the surface accurately models fluid membranes, then the solute's partition coefficient measured on a surface should be the same as the solute's partition coefficient measured on a liposome surfaces of the same lipid mixture.

One preferred embodiment of the present invention is directed to a new method combining liquid chromatography and mass spectrometry for the simultaneous determination of dissociation constants (pKa) of multiple chemical species. The method allows rapid pKa measurements of a wide variety of compounds with high accuracy and resolution. This rapid determination of both bulk and interfacial pKa's meets the increasing demand from both industrial and academic fields: with the rapid development of synthetic techniques for the preparation of large numbers of new chemicals (combinatorial chemistry) over the past few years, millions of potential new drug candidates are created every year, and the determination of a parameter like interfacial pKa is critical for quantitative structure-activity relationships (QSAR) studies, and the world wide drug discovery effort.

One embodiment of the present method involves the use of compound-dependent non-specific binding (as opposed to "specific binding") to differentiate two or more compounds in a test solution. Specific binding is the affinity exhibited between a receptor molecule and a compound wherein the receptor molecule includes a defined binding locus that discriminately binds those compounds which have a predetermined chemical structure. Compounds not having the predetermined chemical structure do not bind with the binding site of the receptor molecule. "Compound-dependent non-specific binding" as used herein refers to that affinity interaction between a compound and a surface that does not have a specific discriminative binding locus for that compound, but rather the binding derives from the concomitant hydrophobic and/or hydrophillic interactions between the surface and the compound. Non-specific binding between a surface and a compound is "compound-dependent" in that, for any one surface, different compounds will interact and bind with such surface to varying degrees based upon the chemical structure and hydrophobic/hydrophillic nature of the compound.

Various covalently bound stationary phases can be used as the test surface for performance of this invention. For example, chromatographic material can be employed, whether commercially available (C18, C8, C4 or other available chromatographic material) or material specifically designed and developed for a particular application or investigation, using mobile phases ranging from highly polar to non-polar. One preferred group of surfaces are so-called membrane mimetic surfaces. The term "membrane mimetic surface" as used in describing and defining the present invention refers to any surface bearing immobilized amphiphilic molecules (i.e., those having both lipophilic and hydrophilic portions) capable of exhibiting some affinity for or otherwise interacting with a solute (e.g., a test or control compound) in a fluid phase in contact with the surface. The term is intended to encompass a broad scope of commercially available stationary phases detailed for use in chromatographic applications. Preferred membrane mimetic surfaces are those described in U.S. Pat. No. 4,931,498, specifically incorporated herein by reference. The choice of the chromatographic material will basically depend on the type of compounds to be analyzed, as well as which type of surface/solute interactions are under investigation.

The detection device coupled to the chromatographic system (or otherwise used in performance of the present method) is a detector that produces signals/data that allow identification and quantification of detected compounds alone or in mixtures with other compounds. Exemplary of such detectors is a mass spectrometer, preferably run in a mild ionization mode such as electrospray ionization (ESI) or Atmospheric Pressure Chemical Ionization (APCI) and with either magnetic/electric sector or quadruple rods as mass filters. Other examples of such detectors include those based on infrared spectroscopy (e.g., FTIR) and those based on nuclear magnetic resonance spectroscopy (NMR).

The mixture of compounds to be analyzed is injected onto the column as a solution, preferentially in the solvent used for the mobile phase but a different solvent can be used instead if confronted with solubility problems, at a concentration that does not exceed the loading capacity of the column in question (for a 3×0.46 cm column, the sample concentration typically ranges from 0.5 to 1.0 $\mu g/\mu l$ ). Overloading the column will result in inaccurate retention times, and consequently the resulting pKa calculations will be erroneous. The mobile phase composition can be determined according to the chemical nature of the compounds to be analyzed. For example, in the case of reverse phase HPLC, a mixture of aqueous acetonitrile and sodium phosphate buffer can be used. The pH of the mobile phase can range from 2 to 12, typically ranging between pH=2.0 and pH=10.0. The number of necessary runs and the mobile phase pH increments will be dependent on the compounds under investigation, and can be determined on a case by case basis to assure maximum data accuracy and resolution. The LC flow rate will be set so that the measurement of the capacity factors takes place in a reasonable amount of time. The wavelength of the HPLC detector (photo diode array, PDA) will be set such that the UV cut-off of the mobile phase is taken into consideration, to maximize the quality and resolution of the chromatogram. The use of a tandem mass spectrometer (MS/MS) may be required for more complex cases where the identification of the compounds eluting from the column is not possible after a single mass spectrometric analysis.

The high sensitivity of the MS detector allows the instantaneous identification of mixtures of compounds. The data from the MS analysis will be correlated to that from the PDA detector of the LC system, resulting in the assignment of a retention time for each and every compound detected. The data can be collected electronically and used as input for one or more algorithms based on the equations derived above for calculating both the bulk and interfacial pKa's for each compound of interest.

One major advantage of the preferred method of this invention is that it allows very fast and simultaneous determination of $^{bulk}$pKa and $^{surface}$pKa for multiple compounds using small amounts of said compounds. A mixture 100 or more compounds can be injected and detected as they elute from the chromatographic system. In theory, depending on the loading capacity of the column, a mixture of up to 1000 compounds can be analyzed. Data processing and computation of both bulk and interfacial pKa's for these compounds can be completed within a short time period.

Variables other than pH may be changed with respect to the mobile phase to allow determination of physical/chemical properties of test compounds. One such variable that may be manipulated is the temperature of the mobile phase. At a set temperature, a test compound will have specific binding characteristics with respect to a surface. As the temperature is varied, such binding characteristics also vary. Thus, in one embodiment the present method can be employed wherein the temperature, rather than the pH, is varied and the binding properties of each compound are evaluated over a range of temperatures.

Other devices finding use for implementing the process of this invention include microchips/MS and capillary electrophoresis/MS. Microchips are a planar glass substrate etched with a channel network. They represent the ability to miniature traditional "benchtop" separation methods with the advantages of speed, automation, and volumetric reduction of sample and waste. The successful interfacing of microchips and mass spectroscopy (MS) has opened another application of high-throughput MS analysis in screening.

Capillary electrophoresis (CEC), a hybrid of HPLC and CE, constitutes a novel technique for the separation field. In CEC, the packed capillary column serves as the injector, pump, separation column and detector cell. CEC has high efficiency for the separation of both neutral and charged compounds, which is especially suitable for the method described in this invention. A plug-like electro-osmotic flow (EOF) enables CEC to separate neutral molecules without the use of surfactants, and makes CEC more amenable to coupling with mass spectrometry. Capillary electrophoresis was used to determine interfacial pKa's of acidic, basic, and amphoteric pharmaceuticals like verapamil, at 9.8 micromole detection limit. This method was also applicable to a mixture of two components. The method can be coupled to MS in the same fashion as it has been described for LC/MS.

For purposes of the present invention, it is not necessary that the equilibrium of the test compounds between a liquid phase and the surface phase be accomplished using a binding surface that is attached to a stationary phase contained within a column. Other techniques may be used to provide partition of the test compounds between the liquid phase and surface phase. As an example of an embodiment for such alternative techniques, the binding surface (whether in the form of an immobilized artificial membrane, liposomes, cells or other surfaces providing compound-dependent affinity for the test compounds) is associated with microtiterplates to which mobile phases, for example, at various pH levels and two or more test compounds are added. The test compounds are allowed to equilibrate between the bulk phase and the surface phase, and the supernatant may be removed and injected in a mass spectrometer to determine the concentration of the test compounds present at the pH levels tested. From this data, the amount of test compound in surface phase is extrapolated at the various pH levels, thereby allowing calculation of physicochemical properties of the test compounds.

In another embodiment of the present method, the binding surface is bound directly to the inner surface of a column (as opposed to having the binding surface attached to a stationary phase such as silica which is packed into the column), and the mobile phase containing two or more test compounds is injected into the column and the test compounds are allowed to equilibrate with the binding surface within the column. After equilibration of the test compounds between the bulk phase and the surface phase, the mobile phase solution is tested to determine the physicochemical characteristics desired, such as the pKas. In this embodiment, the pH level of the mobile phase is varied such that the equilibrium constants of the test compounds at varying pH levels are determined. Such variance of the pH level can be accomplished by using a series of distinct mobile phases at various set pH levels, or through use of a pH gradient system designed such that the pH levels gradually change during the course of a single test injection.

The conventional thinking regarding equations 7 and 8 is that $k'_{HA}$ and $k'_{A^-}$ (the capacity factors of the completely ionized and unionized species) are constants that have to be determined experimentally in order to calculate $^{bulk}pKa$ and $^{surface}pKa$. This requires that the mobile phase have a pH that is 2 pKa units higher or lower than the test compound. This is problematic because it may require use of pH's greater than 8–9, which in the case of some test surfaces causes deterioration. Using the present method, we have determined that it is not necessary to determine these constants. If sufficient data are collected (no matter what the pH range is), non-linear curve fitting techniques can be used to fit three parameters ($^{bulk}pKa$, $^{surface}pKa$ and $k'_{HA}$ (or $k'_{A^-}$, depending on whether you use Eq. 7 or Eq. 8)) instead of two ($^{bulk}pKa$ and $^{surface}pKa$). Indeed, such methods were used in generating data shown in the Examples found below.

Retention time is not the only affinity-based parameter of interest. Other statistical parameters characteristic of chromatographic peaks may be used. For instance, parameters such as the peak width at half height (peak width), the four moments (mean, variance, skewness and kurtosis) may provide valuable data for evaluation and determination of physicochemical values of compounds. The mean is the average or the center of the distribution, and the variance describes the dispersion or shape of the distribution. The skewness characterizes the degree of asymmetry of a distribution around its mean. A positive value of skewness signifies a distribution with a right tailing, likewise, a negative value signifies that the distribution has more negative points toward the left. Kurtosis measures the relative peakedness or flatness of a Gaussian distribution. The conventional thinking in chromatography is that peak retention time is the key parameter to differentiate two compounds under the assumption that all chromatograms are perfect Gaussians. However, two compounds with identical peak retention times may have different dispersions. In this case the peak width is the second parameter that can help distinguish between these two compounds. Similarly, the other parameters can further aid in fine tuning the differentiating process for non-Gaussian chromatograms.

One example of the importance of peak widths as an affinity-based parameter relates to Membrane Affinity Fingerprints (MAFs). The membrane binding properties of test compounds can be calculated, or they can be determined empirically with use of, for example, liposomes, immobilized artificial membranes (such as those described in U.S. Pat. No. 4,931,498, the disclosure of which is incorporated herein by reference), Langmuir Blodget films, computer chips or similar devices with immobilized lipids, capillary zone electrophoresis columns coated with membrane lipids, and the like. In the case of immobilized artificial membranes (IAMs), the numerical values characteristic of membrane affinity are determined chromatographically using an aqueous mobile phase and a stationary phase comprising a membrane mimetic surface as defined in U.S. Pat. No. 4,931,498. Membrane binding properties of a set of test compounds of unknown biological activities are compared to the membrane binding properties of control compounds having known in vivo biological activity to assess the probability that the test compounds will exhibit one or more biological activities in vivo. For each control compound there is a defined and ordered set of numerical values characterizing a biologically relevant interaction (e.g., affinity) of that compound with each of the selected membrane mimetic surfaces.

The ordered set of numerical values for each control compound or each set of control compounds (i.e., a "training set") can be represented by the expression $<C_1, C_2, \ldots, C_n>$ wherein n is the number of membrane mimetic surfaces identified and used in the screening method. A similar ordered set of numerical values $<T_1, T_2, \ldots, T_n>$ for each test compound characteristic of its biologically relevant interaction with each of the respective membrane mimetic surfaces is determined. The set of numerical values for each test compound is then compared with the set of respective values for the control compounds, and the biological properties of those control compounds having ordered sets of numerical values best matching the respective numerical values in the ordered set of values for the test compound are identified. Pattern matching using vector calculus, multivariate analysis or principal component analysis of the numerical values characteristic of the test compounds and the control compounds allows comparison of the membrane binding properties of the test compounds and each of the control compounds or, if the control compounds all have a common biological activity/property, average or mean membrane binding values of the set of control compounds for each membrane mimetic surface.

This method is primarily based on the relative affinities (reflected by the retention times) of the test compounds for the respective IAM surfaces. However, retention time is not the only parameter of importance for MAF predictions. In an independent study, 13 compounds were evaluated for hallucinogenic activity against a hallucinogen mean MAF ($MAF^H$) vector. These 13 compounds were evaluated in a blind study, i.e., no structural information, no in vitro data, and no in vivo data were provided. The hallucinogen $MAF^H$ was established using four IAM surfaces ($^{ester}$IAM.PC$^{C10/C3}$, $^{ester}$IAM.PE$^{C10/C3}$, $^{ester}$IAM.PS$^{C10/C3}$, and IAM.SM$^{C10/C3}$). One of the compounds in the study (BDFA) turned out to be a false positive: it was predicted to be active based on the fact that its order of elution on all four surfaces matched that of the $MAF^H$ vector. In vivo studies carried out after the MAF prediction revealed that BDFA was actually inactive. FIG. 5 shows the chromatographic representation of hallucinogen $MAF^H$ (top graph); the bottom graph shows the chromatographic fingerprint of BDFA superimposed on that of the hallucinogen $MAF^H$ vector. The peak widths of BDFA on $^{ester}$IAM.PS$^{C10/C3}$, and IAM.SM$^{C10/C3}$ are much larger than the corresponding peak widths of the hallucinogen $MAF^H$. BDFA thus provides direct evidence that peak widths are useful for predicting in vivo activity. Peak widths which evaluate the on-off kinetics of drug membrane interactions can be used as another parameter when making predictions.

Further Examples

Figure 6:
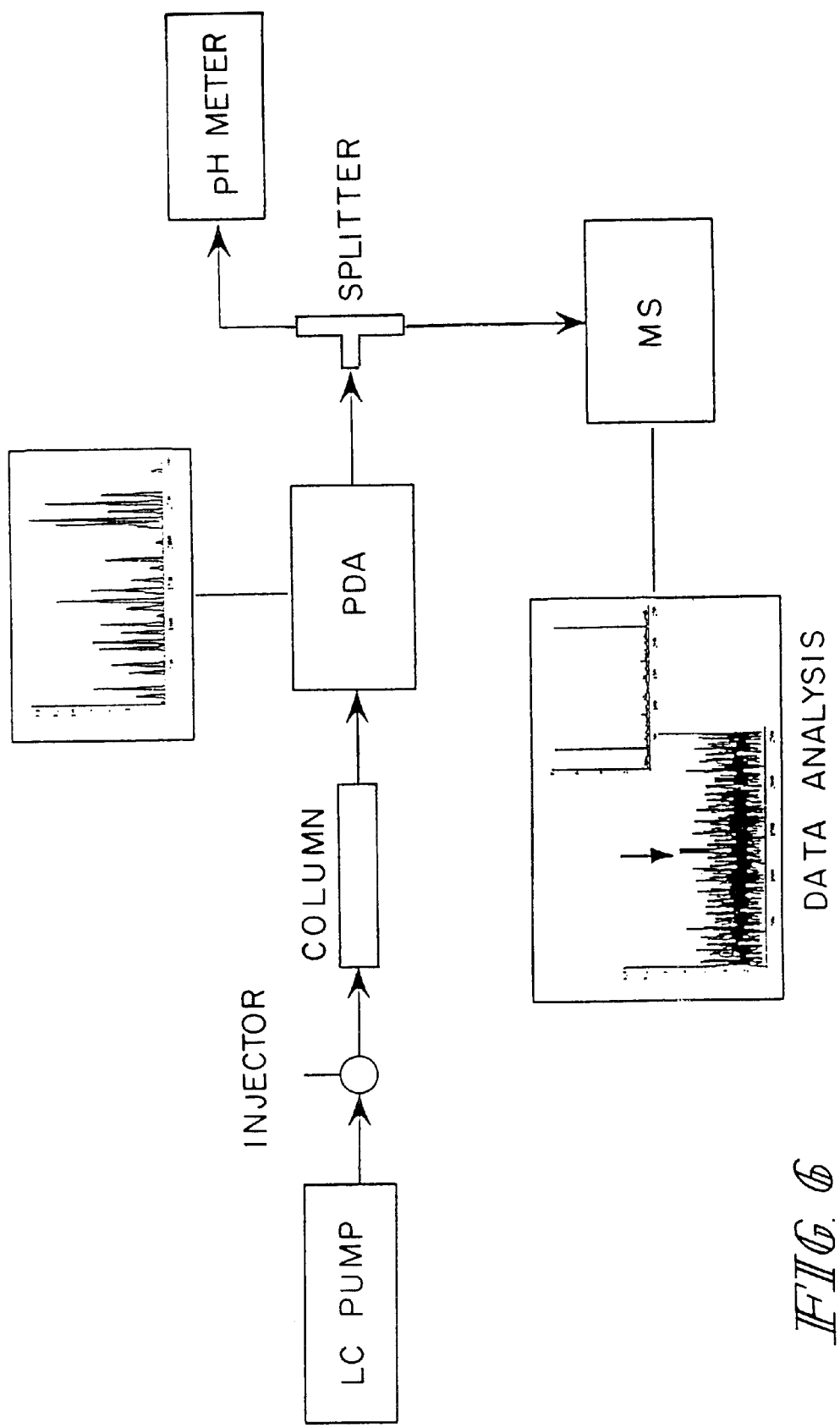
FIG. 6 is a schematic illustration of an LC/MS system useful for carrying out preferred embodiments of this invention.

A preferred embodiment of the instrumental system of the present invention is depicted in FIG. 6. In this system, mobile phase is pumped by a liquid chromatography pump (LC Pump) in fluid communication with a chromatographic column. A compound to be tested is injected into the mobile phase upstream (i.e., towards the LC Pump) of the column, and flows over the column where the test compound will interact with the stationary phase of the column. After passing through the column, the mobile phase/test compound passes into a photo diode array detector (PDA) for chromatographic detection. After passing through the PDA, the mobile phase/test compound flow is split, with a portion of the mobile phase/test compound directed to a pH meter for determination of the pH of the mobile phase and a second portion directed to a mass spectrometer for chemical identification. The pH meter is preferably an "in-line" type of pH system (i.e., a system that is in constant or near-constant fluid communication with the chromatographic system), such as the Micro Flow Through pH systems available from Lazar Research Laboratories, Inc. A system similar to that depicted in FIG. 6 was used to perform the analyses described hereinafter.

Phosphate Buffer Solution

A Phosphate Buffer Saline (PBS) solution was prepared by dissolving 0.2 g of potassium phosphate monobasic, 1.15 g of sodium phosphate dibasic and 2.922 g of sodium chloride in 1 L of distilled water. This produced a PBS buffer with a 0.01 M phosphate, 0.067 M salt and pH around 7.5. The pH of the buffer was adjusted with 1N sodium hydroxide or 6N hydrogen chloride solutions.

pH Meter Calibration

The pH meter was calibrated using two standard buffer solutions and the calibration was evaluated using a third standard buffer solution. For example, if the pH to be measured was in the range of 4 to 8, the standard buffer solutions with pH=4 and pH=7 were used to calibrate pH meter. A pH=8 buffer solution was used to evaluate the calibrating process. A reading error within pH±0.04 was considered a good calibration.

In-line pH Measurement

A Micro Flow Through pH system, purchased from Lazar Research Laboratories, Inc., was used for in-line pH monitoring.

Sample Preparation.

The test compounds were divided into two groups: acidic compounds and basic compounds. The acidic group contained 5 compounds and the basic group contained 12 compounds. The compounds were dissolved in DMSO-PBS buffer (30:70 volume ratio). The sample concentration was 0.05 $\mu$g/$\mu$l for the basic group and 0.121 $\mu$g/$\mu$l for the acidic group.

Standard Compounds

A set of standard compounds was used to monitor column degradation. We chose warfarin (acid) and scopolamine (base) as the standard compounds. The standard samples were prepared in the same manner as the working samples at a concentration of 0.3 $\mu$g/$\mu$l.

LC/MS Conditions

The LC/MS system comprised a Hewlett Packard HPLC (HP 1100 series) interfaced with an Esquire MS spectrometer. The HPLC had two binary pumps and a Photo Diode Array detector (PDA). The mobile phase was a 0.01 M PBS solution and the flow rate was set up to 1 ml/min. The mobile phase pH was adjusted to meet experimental requirements.

The Esquire MS is equipped with an ESI source and a Daly Array (DA) detector. The positive mode was used in the entire experiment.

Chromatographic Columns

The data was collected on 4.6×30 mm $^{ester}$IAM.PC$^{C10/C3}$ columns. Four $^{ester}$IAM.PC$^{C10/C3}$ columns were used to collect all the experimental data.

Data Collection

The test compounds were injected as two distinct mixtures (acidic and basic compounds) to avoid acid/base interactions during the chromatographic runs. Each group was run under 15 mobile phase pH conditions, ranging from pH=4.16 to pH=10.42. The retention time ($t_r$) was determined for each compound and the corresponding capacity factor $k'_{app}$ was calculated. Between each run, column degradation was evaluated by running the standard compounds at pH=7.4. Table 1 lists the raw data for one of the test compounds (Sulfadimethoxine).

The data was collected according to the following sequence:
1. The standard compounds were run at pH=7.4 (to monitor column degradation)
2. The test compound mixture (acid group) was run at the desired pH
3. The test compound mixture (base group) was run at the same pH
4. The sequence was repeated The pH values were recorded with an in-line pH meter.

Data Analysis

The retention time of each compound was determined using the Esquire Data Analysis software. The capacity factors $k'_{app}$ were calculated using the equation: $k'_{app}=(t_r-t_0)/t_0$ where the $t_r$ is the retention time, and $t_0$ is the dead time. The final $^{surface}$Ka and $^{bulk}$Ka were calculated by nonlinear least square curve fitting of the following equations:

Basic compounds:

$k'_{app}=k'_{HA}([H^+]+^{surface}K_a)/([H^+]+^{bulk}K_a)$ (Eq. 7 as shown above).

Acidic compounds:

$k'_{app}=k'_A{}^-([H^+]/^{surface}K_a+1)/([H^+]/+^{bulk}K_a+1)$ (Eq. 8 as shown above).

[H$^+$] was calculated from the mobile phase pH values used for the experiment. The fitting parameters were $k'_A{}^-$, $^{surface}K_a$, and $^{bulk}K_a$ for the acidic compounds and $k_{HA}$, $^{surface}K_a$, and $^{bulk}K_a$ for the basic compounds.

The nonlinear fitting function is from the commercial software S-PLUS (MathSoft). Briefly, the function tries to estimate the parameters to minimize the sum of the squared differences between the response and the prediction. We collected data at 15 different pH values. Only the data collected at pH's that did not cause significant column degradation were used for the curve fitting. Like all silica based chromatography material, Immobilized Artificial Membranes (IAM's) are unstable in the presence of chemically basic mobile phase, and column lifetimes decrease under these conditions. Thus it is not possible to continuously perfuse IAM columns with basic mobile phases for extended periods of time. Mobile phases with pH=8.81 and 10.42 caused the chromatographic material to degrade. Thus, the data collected under these conditions was not used for the determination of $^{bulk}$pKa and $^{surface}$pKa. In addition, the set of data at pH=4.53 was not used either because the chromatographic column used to collect the data showed signs of degradation (the column had been used previously for another study). Thus, we felt that the data was not reliable. In summary, 12 points were used to curve fit the data.

Figure 7:
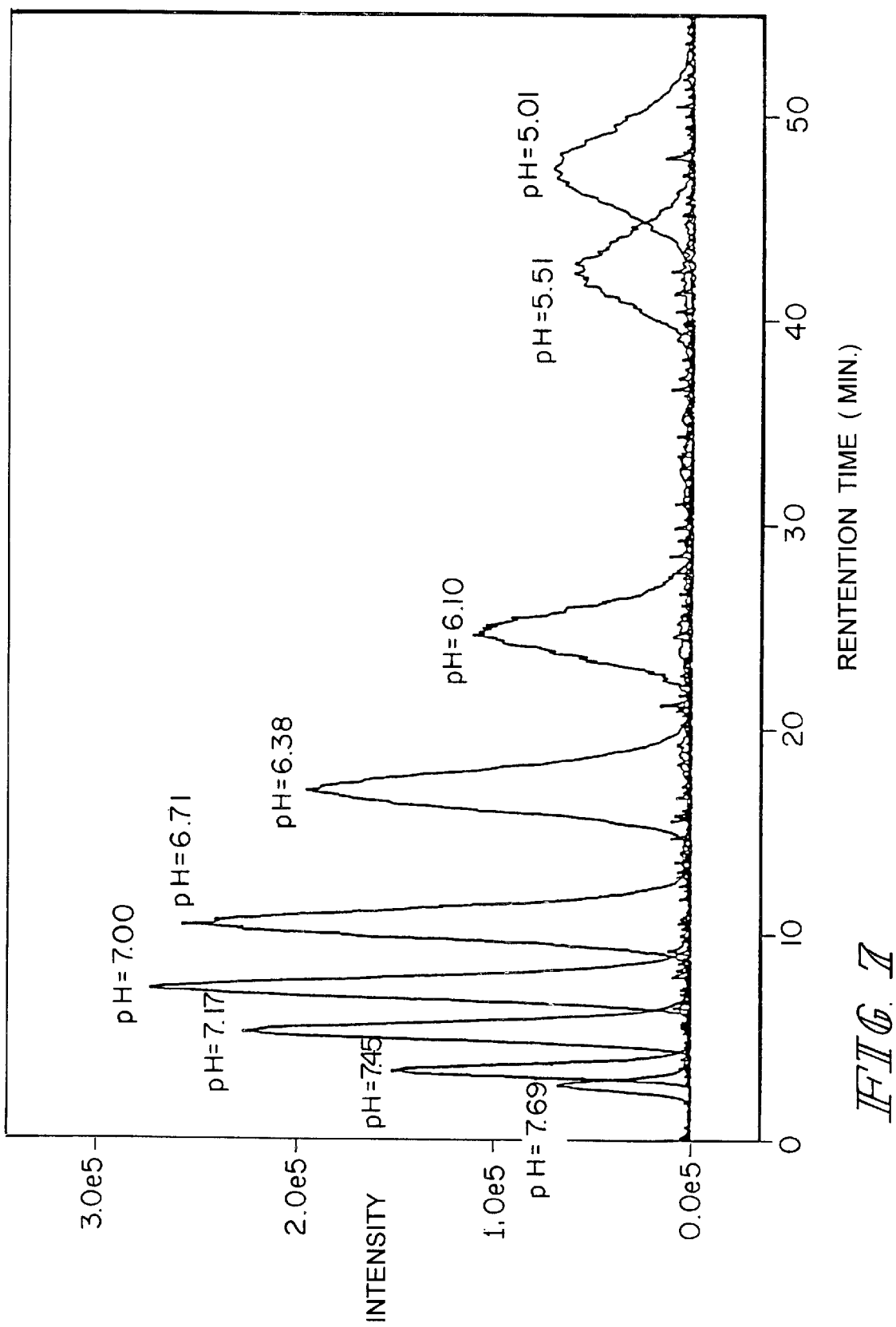
FIG. 7 is a set of chromatograms of a test compound, sulfadimethoxine, at various mobile phase pH conditions.

For each compound, the retention time ($t_r$) was determined and the corresponding capacity factor ($k'_{app}$) was calculated under various mobile phase pH conditions. Table 1 summarizes the chromatographic experimental data collected for sulfadimethoxine. Similar data was collected for the rest of the test compounds (data not shown). FIG. 7 graphically illustrates how the elution time of a test compound (Sulfadimethoxine) is affected when the pH of the mobile phase varies (for clarity purposes, only selected pH data are shown). The raw data (acquired at pH's ranging from 4.05 to 8.06) were used to determine $^{bulk}$pKa and $^{surface}$pKa. The results are listed in Table 2.

TABLE 1

Capacity Factor ($k'_{app}$) of Sulfadimethoxine on IAM.PC Surface as a Function of pH.

| pH | $t_0$(min.) | $t_r$(min.) | $k'_{app}$ |
|---|---|---|---|
| 4.05 | 0.38 | 57.40 | 152.07 |
| 4.53 | 0.35 | 47.82 | 131.83 |
| 5.01 | 0.35 | 46.28 | 131.23 |
| 5.51 | 0.35 | 41.28 | 116.77 |
| 6.10 | 0.35 | 24.35 | 67.79 |
| 6.38 | 0.35 | 16.83 | 46.54 |
| 6.71 | 0.35 | 10.30 | 28.10 |
| 7.00 | 0.35 | 7.25 | 19.48 |
| 7.17 | 0.35 | 5.13 | 13.49 |
| 7.45 | 0.35 | 3.27 | 8.24 |
| 7.69 | 0.35 | 2.62 | 6.40 |
| 7.91 | 0.35 | 2.07 | 4.85 |
| 8.06 | 0.35 | 1.60 | 3.52 |
| 8.81 | 0.35 | 1.36 | 2.84 |
| 10.42 | 0.35 | 0.60 | 0.71 |

TABLE 2

Comparison of Reference pKas with Experimental pKas

| drug name | $^{bulk}$pKa1 (Ref.) | $^{bulk}$pka2 (Ref.) | Conditions | $^{bulk}$pKa (Exp.) | $^{surface}$pKa (Exp.) |
|---|---|---|---|---|---|
| Bases mido-drine | 7.80 | | 0.3% aq. soln | 6.65 | 6.18 |
| linco-mycin | 7.5 | | | 7.54 | 6.28 |
| scopol-amine | 7.55 | | | 7.48 | 6.43 |
| tera-zosin | 7.1 | | 0.1 N NaOH | 6.65 | 6.17 |
| doxyl-amine | 7.64 | 9.20 | | 7.93 | 6.72 |
| nalme-fene | 7.63 | | | 7.81 | 6.88 |
| lido-caine | 7.86 | | | 7.69 | 6.3 |
| nalor-phine | 7.8 | | | 7.63 | 6.04 |
| nalox-one | 7.94 | | | 7.84 | 6.24 |
| bru-cine | 6.04 | 11.70 | | 7.9 | 6.55 |

TABLE 2-continued

Comparison of Reference pKas with Experimental pKas

| | drug name | $^{bulk}pKa1$ (Ref.) | $^{bulk}pka2$ (Ref.) | Conditions | $^{bulk}pKa$ (Exp.) | $^{surface}pKa$ (Exp.) |
|---|---|---|---|---|---|---|
| | minaprine | 7.05 | 4 | | 6.75 | 5.75 |
| | ajmaline | 8.1 | | 20° C., DMFA/H$_2$O-80% | 7.43 | 6.75 |
| Acids | warfarin | 5.05 | | | 5.43 | 7 |
| | sulfamethoxazole | 5.6 | | | 5.82 | 7.55 |
| | ofloxacin | 5.74 | 7.9 | | 6.84 | 7.32 |
| | nalldixic acid | 6.02 | | | 6.03 | 7.54 |
| | sulfadimethoxine | 6.7 | | | 6.02 | 7.64 |

Overall, the $^{bulk}pKa$'s determined experimentally are in good agreement with the $^{bulk}pKa$ values found in the literature. The difference can be accounted for by the fact that literature and experimental pKa values may have been determined under different conditions (bulk media). Virtually no information regarding the experimental conditions used for determining $^{bulk}pKa$'s are given in the literature sources that we consulted. However, for a few test compounds (midodrine, terazosin, and ajmaline) the experimental conditions were specified. All three are different from the conditions used for the collection of the data presented in the present application. In all three instances, the $^{bulk}pKa$'s obtained experimentally do not perfectly match the values given in the literature. This is expected since the degree of ionization of a compound (thus its $^{bulk}pKa$) is affected by the composition of the bulk medium. Although no information regarding the conditions under which the reference $^{bulk}pKa$'s were determined is available for the rest of the test compounds (except for the polyvalent acids/bases), the values (experimental & reference) are in good enough an agreement to validate the method.

Note that in the case of polyvalent species (doxylamine, brucine, minaprine and ofloxacin), which have more than one ionizable group, the $^{bulk}pKa$ values obtained experimentally do not agree with the literature values. The reason is that the data was curve fitted to equations that were derived for monovalent species. For polyvalent species other equations are needed. The $^{bulk}Ka$ (and $^{surface}pKa$) values calculated for the divalent acids and bases are incorrect because they were derived from the wrong equations.

The $^{surface}pKa$ values for the test compounds used in the experiment have not been published. Thus the accuracy of the values derived from the method described in the present invention may not be easily evaluated. However, since Eq. 7 and Eq. 8 are true, and $^{bulk}Ka$'s are correct, the numerical values obtained for $^{surface}pKa$ must be acceptable (except for polyvalent compounds and compounds run in different conditions, as explained above). Note that for the basic compounds, the $^{surface}pKa$'s are 0.75 to 1.75 pKa units lower than the $^{bulk}pka$'s. Conversely, for the acids, the $^{surface}pKa$'s are 0.95 to 1.95 pKa units higher than the $^{bulk}pka$'s. This is consistent with the fact that at the chromatographic surface (phosphatidylcholine ligands), the predominant species is the non ionized form of the compounds. In other words, the acid/base equilibrium at the chromatographic surface is in favor of the unionized species. The fact that the acid/base equilibrium constants vary by a factor of 10 to 100 between the bulk media and the IAM surface is significant since it gives an indication of the ionization behavior of the compounds under investigation at the membrane surfaces; e.g., it can give insights into their biological activities.

We claim:

1. A method for determining a dissociation constant for each one of at least a portion of a set of compounds, said method comprising:

dissolving said set of compounds in an aqueous medium having a predetermined composition, to form a test solution containing the set of compounds;

contacting said test solution at a predetermined temperature with a membrane mimetic surface exhibiting a non-specific compound-dependent affinity for at least the portion of the set of compounds;

measuring a parameter dependent on the non-specific affinity of the surface for each one of at least the portion of the set of compounds in the test solution after contact of the solution with the surface under the predetermined set of conditions, said parameter measurement including identification of each compound exhibiting said affinity-dependent parameter; and calculating the dissociation constant for each one of at least the portion of the set of compounds using the measured parameter.

2. The method of claim 1 further comprising the steps of dissolving the set of compounds in a second aqueous medium, each medium having a unique hydrogen ion concentration, to form first and second test solutions, each of said test solution containing the set of compounds;

contacting each of said test solutions at a predetermined temperature with a surface exhibiting a compound-dependent affinity for at least the portion of the set of compounds;

measuring a parameter dependent on the affinity of the surface for each one of at least the portion of the set of compounds in each test solution after contact of the solution with the surface under the predetermined set of conditions; and calculating the dissociation constant for each one of at least the portion of the set of compounds using the measured parameter.

3. The method of claim 2 wherein the step of contacting each test solution with the surface is carried out in a high pressure liquid chromatography system using a stationary phase and a liquid mobile phase where the stationary phase comprises the surface and the liquid mobile phase has the same composition as the respective aqueous medium used to form each test solution.

4. The method of claim 3 wherein the affinity-dependent parameter is a statistical parameter characteristic of a chromatographic peak.

5. The method of claim 3 wherein the affinity-dependent parameter is retention time, peak width, peak mean, peak variance, peak skewness or peak kurtosis.

6. The method of claim 3 wherein each aqueous medium further comprises an organic modifier.

7. The method of claim 3 wherein the affinity-dependent parameter is the retention time for each compound in at least the portion of the set of compounds.

8. The method of claim 2 wherein the step of contacting each test solution with the surface is carried out by liquid chromatography using a stationary phase and a liquid mobile phase where the stationary phase comprises the surface and the liquid mobile phase is a pH gradient of the respective aqueous medium used to form each test solution.

9. The method of claim 8 wherein the affinity-dependent parameter is the retention time each compound in at least the portion of the set of compounds.

10. The method of claim 6 or claim 8 wherein the affinity-dependent parameter is the width of the peak for each compound as it is eluted from the stationary phase.

11. The method of claim 3 wherein the compounds in the test solution are at substantially equimolar concentrations and the step of contacting each test solution with the surface is carried out by contacting a predetermined volume of each test solution with a predetermined area of said surface, and the affinity-dependent parameter for each compound is the resulting concentration after equilibrium contact with the surface of each compound in each test solution.

12. The method of claim 3, 6, 7, 8, 9, or 11 wherein the surface is a surface comprising phospholipids covalently bound to a solid substrate.

13. The method of claim 3 wherein the hydrogen ion concentration of each of the first and second aqueous media is such that the pH of each of the test solutions is between about pH2 and about pH12.

14. The method of claim 6 or 7 wherein the pH of each of the first and second aqueous media is between about pH2.0 and about 12.0.

15. The method of claim 1 wherein the measuring step comprises mass spectrometric analysis of each solution after contact with the surface.

16. The method of claim 3 wherein one or more compounds of said set of compounds has a known dissociation constant.

17. A method for determining a dissociation constant for each one of at least a portion of a set of compounds, said method comprising:

dissolving said set of compounds in a plurality of liquid media, each medium having a predetermined composition, to form a multiplicity of test solutions, each of said test solutions containing the set of compounds;

contacting each of said test solutions with a membrane mimetic surface under a predetermined set of conditions of temperature and pressure, said surface exhibiting a non-specific compound-dependent affinity for each one of at least the portion of the set of compounds;

measuring a parameter dependent on the non-specific affinity of the surface for each one of at least the portion of the set of compounds in each test solution after contact of the solution with the surface under the predetermined set of conditions; and calculating the dissociation constant for each one of at least the portion of the set of compounds using the measured parameter.

18. The method of claim 17 wherein the affinity-dependent parameter is a statistical parameter characteristic of the chromatographic peak.

19. The method of claim 17 wherein the affinity-dependent parameter is retention time, peak width, peak mean, peak variance, peak skewness or peak kurtosis.

20. The method of claim 17 wherein each respective aqueous medium has a unique hydrogen ion concentration.

21. The method of claim 17 wherein each respective aqueous medium has a unique ionic strength.

22. The method of claim 17 wherein the composition of each aqueous medium is identical and each test solution is contacted with the surface at a unique pressure.

23. The method of claim 1 wherein the membrane mimetic surface comprises phospholipids covalently bound to a solid substrate.

24. The method of claim 17 wherein the parameter for each compound is measured using mass spectrometry, Fourier-transform infrared spectroscopy, or nuclear magnetic resonance.

25. The method of claim 17 or 22 wherein the step of contacting each test solution with the surface is carried out by liquid chromatography using a stationary phase and a liquid mobile phase, wherein the stationary phase comprises the surface and the liquid mobile phase has the same composition as the respective aqueous medium used to form each test solution.

26. The method of claim 25 wherein the affinity-dependent parameter is the retention time for each one of the portion of the set of compounds.

27. The method if claim 20 or 21 wherein the step of contacting each test solution with the surface is carried out by liquid chromatography using a stationary phase and a liquid mobile phase, wherein the stationary phase comprises the surface and the liquid mobile phase has the same composition as the respective aqueous medium used to form each test solution.

28. The method of claim 27 wherein the affinity-dependent parameter is the retention time for each one of the portion of the set of compounds.

29. The method of claim 17 wherein the step of contacting each solution with the surface is carried out by liquid chromatography using a stationary phase and a liquid mobile phase wherein the stationary phase comprises the surface and the liquid mobile phase is a pH gradient of the respective aqueous medium used to form each test solution.

30. The method of claim 17 wherein the compounds in the test solution are at substantially equimolar concentrations and the step of contacting each test solution with the surface is carried out by contacting a predetermined volume of each test solution with a predetermined area of said surface, and the affinity-dependent parameter for each compound is the resulting concentration after equilibrium contact with the surface of each compound in each test solution or the resulting concentration after equilibrium contact with the surface of each compound on the surface.

31. The method of claim 17 wherein each respective liquid medium further comprises an organic modifier.

32. A method for determining a temperature-dependent physicochemical value for each one of at least a portion of a set of compounds, said method comprising:

dissolving said set of compounds in an aqueous medium having a predetermined composition, to form a test solution containing the set of compounds;

contacting said test solution at a predetermined temperature with a membrane mimetic surface exhibiting a non-specific compound-dependent affinity for at least the portion of the set of compounds;

measuring a parameter dependent on the non-specific affinity of the surface for each one of at least the portion of the set of compounds in the test solution after contact of the solution with the surface under the predetermined set of conditions, said parameter measurement including identification of each compound exhibiting said affinity-dependent parameter;

contacting the test solution with the surface at a second temperature and measuring the parameter at the second temperature, said first and second measurements acquired by mass spectrometric analysis; and calculating the temperature-dependent physicochemical value for each one of at least the portion of the set of compounds using the measured parameter, wherein the calculation of the temperature-dependent physicochemical value for each one of at least the portion of the set of compounds uses said measured parameter according to a predetermined algorithm.

\* \* \* \* \*